United States Patent
Tennekoon et al.

(10) Patent No.: US 6,673,606 B1
(45) Date of Patent: Jan. 6, 2004

(54) THERAPEUTIC USES FOR MESENCHYMAL STROMAL CELLS

(75) Inventors: Gihan Tennekoon, Wynnewood, PA (US); Andrew J. Coyle, Philadelphia, PA (US); Judith Grinspan, Ardmore, PA (US); Jackie S. Beesley, West Sussex (GB)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 09/833,066

(22) Filed: Apr. 12, 2001

Related U.S. Application Data

(60) Provisional application No. 60/196,473, filed on Apr. 12, 2000, and provisional application No. 60/242,673, filed on Oct. 24, 2000, now abandoned.

(51) Int. Cl.$^7$ ................................................. C12N 5/08
(52) U.S. Cl. ....................... 435/372; 435/325; 435/366; 435/368; 435/377; 424/93.1
(58) Field of Search ............................... 424/93.2, 93.1; 435/325, 368, 375, 377, 391, 372, 366

(56) References Cited

U.S. PATENT DOCUMENTS

| | | | |
|---|---|---|---|
| 5,753,506 A | 5/1998 | Johe | 435/377 |
| 5,851,832 A | 12/1998 | Weiss et al. | |
| 2001/0033834 A1 * | 10/2001 | Wilkison | 424/93.7 |

FOREIGN PATENT DOCUMENTS

| | | |
|---|---|---|
| WO | WO 98/10058 A1 | 3/1998 |
| WO | 99/43286 | 9/1999 |
| WO | 99/56759 | 11/1999 |

OTHER PUBLICATIONS

Roecklein, B.A. et al. Functionally Distinct Human Marrow Stromal Cell Lines Immortalized by Transduction with the Human Papilloma Virus E6/E7 Genes. Blood. Feb. 15, 1995, pp. 997–1005.*

Barres, B.A. et al. Multiple Extracellular Signals are Required for Long–Term Oligodendrocyte Survival. Development. 1993, vol. 118, pp. 283–295.*

Counter, C. M. et al. Dissociation Among In Vitro Telomerase Activity, Telomere Maintenance, and Cellular Immortalization. Proc. Natl. Acad. Sci. Dec. 1998, vol. 95, pp. 14723–14728.*

Bodnar, A. G. et al. Extension of Life–Span by Introduction of Telomerase into Normal Human Cells. Science. Jan. 16, 1998, Vol 270, pp. 349–352.*

Azizi et al., Engraftment and migration of human bone marrow stromal. . . , Mar. 1998, Proc. Natl. Acad. Sci., vol. 95, pp. 3908–3913.*

Prockop et al., Marrow Stromal Cells as Stem Cells for Nonhematopoietic Tissues, Apr. 4, 1997, Science, vol. 276, pp. 71–74.*

Hunter et al., Growth factor responses enriched bipotential glial progenitors, Mar. 1990, pp. 235–248.*

Smith et al., Porcine neural progenitors require commitment to the oligodendrocyte. . . , 2000, Journal of Neuroscience, vol. 12, pp. 2414–2424.*

Eglitis et al., Hematopoietic cells differentiate in both microglia and macrogila in the brain of adult mice, Apr. 1997, Proc. Natl. Acad. Sci., vol. 94, pp. 4080–4085.*

Blakemore et al., Remyelinating the demyelinated CNS, 200 Neural transplantation in neurodegenerative disease. Wiley, Chichester (Novartis Foundation Symposium 231) p 289–301.*

Smith et al., The Formation of New Myelin in the CNS by Transplantation, NeuroScience News, vol. 3, No. 6, 2000.*

Keirstead et al., The Role of Oligodendrocytes and Oligodendrocyte Progenitors in CNS Remyelination, 18069302–15, pp 183–197.*

Sasaki, et al. "Transplantation of an Acutely Isolated Bone Marrow Fraction Repairs Demyelinated Adult Rat Spinal Cord Axons" GLIA 35:26–34 (2001) Wiley–Liss, Inc.

Ferrari, G. et al. "Muscle Regeneration by Bone Marrow––Derived Myogenic Progenitors" Science, Vol 279 Mar. 6, 1998.

A. Coyle et al., "Human Mesenchymal Stromal Cells Can Differentiate Into Oligodendrocyte Lineage In Transplantation Experiments With Rats," Society for Neuroience Abstracts, Abstract No. 415.11, 30$^{th}$ Annual Meeting of the Society of Neuroscience, vol. 26, New Orleans, LA, Nov. 4–9, 2000.

J. Grinspan et al., "Stage–Specific Effects of Bone Morphogenetic Proteins on the Oligodendrocyte Lineage," Neuro Report, vol. 9 No. 7, pp. 1–17. 2000.

S. Ho et al., "Induction of NG108–15 Cells Differentiation by Human Bone Marrow Stromal Cells," Neuro Report, vol. 9, pp. 1365–1369, 1998.

S. Azizi et al., "Engraftment and Migration of Human Bone Marrow Stromal Implanted in the Brains of Albino Rats–Similarities to Astrocyte Grafts," Proc. Natl. Acad. Sci., vol. 95, pp. 3908–3913, 1998.

Barres et al., "Axonal Control of Oligodendrocyte Development", Glial Cell Development, Section 4.1, pp. 71–83.

(List continued on next page.)

Primary Examiner—Deborah J. Reynolds
(74) Attorney, Agent, or Firm—Dann, Dorfman, Herrell and Skillman

(57) ABSTRACT

Human mesenchymal stromal cells can be induced to differentiate into oligodendrocytes and neurons, respectively. For these cell types, therefore, MSCs can be a therapeutic source, either in vitro or in vivo, in the context of treating pathologies of the central nervous system which are characterized by neuron loss, such as Parkinson's disease, Alzheimer's disease and stroke, as well as head trauma, or by dysfunction in ganglioside storage or demyelinization, such as Tay-Sachs disease, G1 gangliosidosis, metachromatic leukodystrophy, and multiple sclerosis.

4 Claims, No Drawings

OTHER PUBLICATIONS

Miyazono et al., "Long–Term Integration and Neuronal Differentiation of Human Embryonal Carcinoma Cells (Ntera–2) Transplanted into the Caudoputamen of Nude Mice", *The Journal of Comparative Neurology*, 376:603–613, 1996 Wiley–Liss, Inc.

B. A. Barres, et al., "A novel role for thyroid hormone, glucocorticoids and retinoic acid in timing oligodendrocyte development", Development 120, 1994, pp. 1097–1108, Great Britain, The Company of Biologists Limited.

David .P. Younkin, et al., "Inducible expression of neuronal glutamate receptor channels in the NT2 human cell line", Proc. Natl. Acad. Sci. USA, 1993, pp. 2174–2178, vol. 90, Neurobiology, USA.

Darwin J. Prockop, "Marrow Stromal Cells as Stem Cells for Nonhematopoietic Tissues", Science, 1997, pp. 1–164, vol. 276, USA.

Oliver Brüstle, et al., "Chimeric brains generated by intraventricular transplantation of fetal human brain cells into embryonic rats", Nature Biotechnology, 1998, pp. 1040–1044, vol. 16, Research, France.

Gabriel V. Ronnett, et al., "Human Cortical Neuronal Cell Line: Establishment from a Patient with Unilateral Megalencephaly", Reports, 1990, pp. 521–636, vol. 248, American Association for the Advancement of Science, USA.

Samuel J. Pleasure, et al., "Pure, Postmitotic, Polarized Human Neurons Derived from NTera 2 Cells Provide a System for Expressing Exogenous Proteins in Terminally Differentiated Neurons", The Journal of Neuroscience, 1992, pp. 1802–1815, vol. 12, No. 5, Society for Neuroscience, USA.

Louis F. Reichardt, et al., "Neurotrophic factors and their receptors", Molecular and Cellular Approaches to Neural Development, 1997, pp. 220–263, Oxford University Press, USA.

Christopher E. Henderson, et al., "Neurite outgrowth from embryonic chicken spinal neurons is promoted by media conditioned by muscle cells", Proc. Natl. Acad. Sci. USA, 1981, pp. 2625–2629, vol. 78, No. 4, Neurobiology, USA.

Sofie R. Kleppner, et al., "Transplanted Human Neurons Derived From a Teratocarcinoma Cell Line (NTera–2) Mature, Integrate, and Survive for Over 1 Year in the Nude Mouse Brain", The Journal of Comparative Neurology, 1995, pp. 618–632, vol. 357, No. 4, Wiley–Liss, Inc., USA.

Thomas Brummendorf, et al., "Structure/function relationships of axon–associated adhesion receptors of the immunoglobulin superfamily", Current Opinion in Neurobiology, 1996, pp. 584–593, vol. 6, No. 5, Current Biology Ltd., USA.

B. A. Barres, et al, "Multiple extracelluar signals are required for long–term oligodendrocyte survival", Development, 1993, pp. 283–295, vol. 118, No. 1, The Company of Biologists, Ltd., Great Britain.

Sôlen Gôkhan, et al., "Generation and Regulation of Developing Immortalized Neural Cell Lines", Methods: A Companion to Methods on Enzymology, 1998, pp. 345–358, vol. 16, Article No. ME980689, Academic Press, USA.

J. C. Louis, et al., "CG–4, A New Bipotential Glial Cell Line From Rat Brain, Is Capable of Differentiating in Vitro into Either Mature Oligodendrocytes or Type–2 Astrocytes", Journal of Neuroscience Research, 1992, pp. 193–204, vol. 31, No. 1, Wiley–Liss, Inc., USA.

Jane E. Bottenstein, et al., "Selective Survival of Neurons from Chick Embryo Sensory Ganglionic Dissasociates Utilizing Serum–Free Supplemented Medium", Experimental Cell Research, 1980, pp. 183–190, vol. 125, No. 1, Academic Press, Inc., Sweden.

Gerard Bain, et al., "Neuronlike Cells Derived in Culture from P19 Embryonal Carcinoma and Embryonic Stem Cell", Culturing Nerve Cells, 1998, pp. 189–211, A Bradford Book, The MIT Press, Cambridge, Massachusetts, London, England.

Steve E. Pfeiffer, et al., "The oligodendrocyte and its many cellular processes", Trends in Cell Biology, 1993, pp. 191–197, vol. 3, No. 6, Elsevier Science Publishers Ltd.

Neeta Singh Roy, et al., "Identification, Isolation, and Promoter–Defined Separation of Mitotic Oligodendrocyte Progenitor Cells from the Adult Human Subcortical White Matter", The Journal of Neuroscience, 1999, pp. 9986–9995, vol. 19, No. 22, Society of Neuroscience, USA.

Gary Banker, et al., "Astrocytes, Oligodendrocytes, and O–2A Progenitor Cells", Culturing Nerve Cells, 1998, pp. 517–530, Massachusetts Institute of Technology.

Titia De Lange, et al., "Unlimited Mileage from Telomerase", Science, 1999, pp. 947–949, vol. 283, No. 5404, American Association for the Advancement of Science. (www.sciencemag.org).

Samuel F. Hunter et al., "Growth Factor Responses Of Enriched Bipotential Glial Progenitors", 1990, pp. 235–248, Elsevier Science Publishers B.V., Galveston, Texas.

P.M. Smith et al., "Porcine Neural Progenitors Require Commitment To The Oligodendrocyte Lineage Prior To Transplantation In Order To Achieve Significant Remyelination Of Demyelinated Lesions In The Adult CNS", European Journal of Neuroscience, 2000, pp, 2414–2424, vol. 12, Federation of European Neuroscience Societies.

Martin A. Eglitis et al., "Hematopoietic Cells Differentiate Into Both Microglia And Macroglia In The Brains Of Adult Mice", Proc. Natl. Acad. Sci. USA, 1997, pp. 4080–4085, vol. 94, Neurobiology. (www.pnas.org).

\* cited by examiner

THERAPEUTIC USES FOR MESENCHYMAL STROMAL CELLS

This is a non-provisional application based on U.S. Provisional application Nos. 60/196,473 filed Apr. 12, 2000 and 60/242,673 filed Oct. 24, 2000, now abandoned.

Funding for this application was Federally provided under Grant No. NA21700.

FIELD OF THE INVENTION

The present invention relates to preparing and using different types of cells to ameliorate pathologies of the central nervous system (CNS) which are associated with the dysfunction or loss of neurons and oligodendrocytes, respectively.

DESCRIPTION OF THE RELATED ART

Two components of the mammalian CNS, oligodendrocytes and neurons, do not readily undergo mitotic division and, hence, are not replaced in vivo upon their loss, occasioned by disease or trauma. For example, Parkinson's disease involves a loss of neurons in a portion of the brain that produces dopamine. The resultant decline in dopamine levels is manifested in the development of muscle tremors, a stiffening of muscles and joints, and an overall lack of coordination. Another neurodegenerative disease, multiple sclerosis (MS), is marked by a breakdown in the axonal sheathing of myelin, constituted by oligodendrocytes, during early post-natal development. This demyelination disrupts signal transmission along the axon, causing vision impairment, loss of coordination, and even memory loss.

The devastating effects of such diseases have motivated research into cell lines and culture conditions that can accommodate in vitro differentiation of cells into neurons and the supporting cells of the CNS, including oligodendrocytes. It has been determined, for example, that rat O-2A cells, the progenitors of oligodendrocytes, can be prompted to differentiate into mature oligodendrocytes by the removal of mitogens from the growth medium. Barres et al., *Development* 120: 1097 (1994). Alternatively, rat O-2A cells will differentiate into mature oligodendrocytes when cultured in a serum-free medium, in the presence of mitogens, if ligands for hydrophobic cell-surface receptors are present, such as thyroid hormones, glucocorticoids and retinoic acid. Id. A human teracarcinoma cell line, designated "NT2," can be differentiated into post-mitotic CNS neurons, by means of a complex regimen of in vitro manipulations, over a period of 6 to 10 weeks. Younkin et al., *Proc. Nat'l Acad. Sci. USA* 90: 2174 (1993).

The differentiation of multipotent neural stem cells is another possible route to obtaining neurons. Thus, U.S. Pat. No. 5,851,832 discloses a subpopulation of constitutively proliferating cells, from the subependymal region lining the lateral ventricles in the forebrain, that are said to be capable of differentiating into a neuronal lineage.

While capable of differentiating into oligodendrocytes or neurons, neural stem cells are difficult to obtain in quantities sufficient for potential therapeutic uses. This fact and the drawbacks associated with known cell lines, such as teracarcinoma-derived NT2 line, have meant that few therapeutic alternatives were available for treating disorders characterized by reduced levels of oligodendrocytes or neurons.

SUMMARY OF THE INVENTION

It is therefore an object of the present invention to provide a source for differentiated oligodendrocytes and neurons, respectively, that is independent of neural stem cells and conventional cell lines.

It is another object of the present invention to provide a workable therapeutic approach toward pathologies, affecting the CNS, that are characterized by the loss of neurons and/or oligodendrocytes.

In accomplishing these and other objects, there has been provided, according to one aspect of the present invention, a method for treating a pathology, characterized by damaged myelin or neurological deterioration, that comprises (A) providing a composition in vitro that consists essentially of (i) mesenchymal stromal cells, or "MSCs," and (ii) a physiologically compatible carrier therefor, (B) exposing the composition to conditions such that the MSCs differentiate into neurons and/or oligodendrocytes, and then (C) allowing the differentiated cells to compensate for neurological deterioration or damaged myelin in a subject suffering from the pathology in question. In a preferred embodiment, the composition is introduced into the nervous system of the subject.

Pursuant to another aspect of the present invention, differentiated cells are prepared by exposing an MSC-containing composition, as described above, to conditions such that the MSCs differentiate in vitro into neurons and/or oligodendrocytes.

In a related vein, the present invention further provides a composition that consists essentially of immortalized mesenchymal stromal cells and a physiologically compatible carrier. Additionally, the invention encompasses a composition that consists essentially of immortalized mesenchymal stromal cells, one or more exogenous genes, and a physiological compatible carrier.

DETAILED DESCRIPTION OF THE PREFERRED EMBODIMENTS

It has been found that mesenchymal stromal cells, stem-like precursors of non-hematopoietic cells, can differentiate into oligodendrocytes and neurons, respectively. Prior to this invention, there was no indication that MSCs could differentiate into oligodendrocytes or neurons. It had been suggested that at least a subset of cells isolated from bone marrow could follow the developmental pathway of astrocytes, another CNS cell type. See Azizi et al., *Proc. Nat'l Acad. Sci. USA* 95: 3908 (1999). But there was no reason to predict heretofore that MSCs would be able to differentiate along a lineage leading to an oligodendrocytic or to a neuronal morphology.

This surprising capability, discovered by the inventor, makes MSCs and MSC-differentiated cells, in accordance with the present invention, a therapeutic resource for treating (A) CNS pathologies characterized by neuron loss, such as Parkinson's disease, Alzheimer's disease, Huntington's disease, and stroke, and (B) metabolic lipid-storage diseases, such as Tay-Sachs, GM1 gangliosidosis, adrenoleukodystrophy, Krabbe's disease, metachromatic leukodystrophy and multiple sclerosis, which involve oligodendrocytic loss. By the same token, the present invention also provides for the use of MSCs and MSC-differentiated cells to ameliorate the neuronal loss brought on by head injury or other trauma.

To these ends, the invention contemplates, in one of its aspects, administering a therapeutically effective amount of MSC or MSC-differentiated cells to a patient in need of either oligodendrocytes or neurons. In this regard, "MSC-differentiated cells" refers to any cell that has differentiated from an MSC, including both immature and mature oligodendrocytes and neurons, respectively. "Therapeutically effective" connotes an amount of MSCs or MSC-differentiated cells that lessens the detrimental effect of ("ameliorates") the CNS disorder in a patient receiving the therapy.

As described below in more detail, MSCs are relatively easy to isolate from aspirates of bone marrow, which can be obtained under local anesthesia. They also are relatively easy to expand in culture, and to transfect with exogenous DNA, as reported in Prockop, *Science* 276: 71 (1997). These advantages, combined with their stem cell-like qualities of in situ migration and pluripotency, recommend MSCs for use, pursuant to the present invention, as vehicles for therapeutic DNA delivery in the context, for example, of treating CNS disorders, such as brain cancer.

Although MSCs themselves can be administered therapeutically, according to the present invention, in many instances it may be more practical to administer MSC-differentiated cells to a patient suffering from a CNS disorder. To this end, MSCs can be differentiated into oligodendrocyte and neurons, respectively, under appropriate culture conditions determined empirically, by adding and removing various trophic factors known to effect neuronal or oligodendrocytal differentiation, thereby mimicking in vivo physiological conditions.

Isolating MSCs From Bone Marrow

For purposes of the present invention, MSCs can be obtained by known methodologies disclosed, for example, by Azizi et al. (1999), supra. To this end, bone marrow can be aspirated from the iliac crest of a donor, who can be the patient to be treated in accordance with the present invention. Bone marrow donors should be screened for hepatitis and HIV. The MSCs then are isolated from the bone marrow, via conventional technology exemplified by Azizi et al. (1999), supra.

By this approach, bone marrow aspirates are diluted with fetal bovine serum (FBS) and centrifuged. The supernatant and interface then are combined, again diluted, and centrifuged. The nucleated cells are then suspended at a desired concentration of FBS and plated onto culture dishes at a desired density. The cells are incubated for about three days, and the non-adherent cells are removed by replacing the medium. After the cultures reach confluency, the cells are lifted by trypsinization. The diluting and replating procedure can be repeated for three to five passages, while platelet-derived growth factor alpha alpha (PDGF-AA; GIBCO/BRL) is added, beginning with the second passage.

Proliferating and Differentiating Neuron Precursor Cells In Vitro

MSCs should be grown on a substrate that enhances proliferation and differentiation. Such a suitable substrate is obtained by the methodology of Gottlieb et al., Culturing Nerve Cells 202–06 (MIT Press, 1998), who coated the bottom of tissue-culture flasks with 0.1% gelatin, yielding a surface that is conducive to proliferating and differentiating neuronal precursor cells. Gottlieb et al. also disclose a culture medium, suitable for effecting MSC proliferation, which is Dulbecco's Modified Eagle's Medium (DMEM) plus glutamine, without pyruvate, and FBS, newborn calf serum, leukemia inhibitory factor (LIF), β-mercaptoethanol, and nucleoside stocks, containing varied concentrations of the 5'-nucleosides in distilled water.

The Gottlieb methodology, employed to proliferate embryonic stem (ES) cells before differentiating them into neurons, is readily adapted to the purpose of stimulating MSC proliferation/differentiation. Other techniques for inducing the proliferation of neuron precursor cell likewise can be adapted to effect MSCs proliferation in vitro, pursuant to the present invention. For example, Brustle et al., *Nature Biotechnology* 16: 1040 (1998), discloses a growth medium which is suitable to this end, containing DMEM, glucose, glutamine, sodium bicarbonate, insulin, human apo-transferrin, progesterone, putrescine, sodium selenite, penicillin/streptomycin, fibroblast growth factor (FGF2), and epidermal growth factor (EGF).

During MSC proliferation, LIF and β-mercaptoethanol levels should be monitored, as both are important in preventing spontaneous differentiation of the MSCs in culture. Also, it is important to monitor culture density and to keep levels within established bounds, that is, 60–70% confluency.

The passaging of MSCs is a straightforward process. After the initial plating of the bone marrow, the MSCs are purified from the hematopoetic cells by utilizing the property of differential adhesiveness, as disclosed in Azizi et al.(1999), supra. Subsequent passage of MSCs is accomplished by means of a standard trypsin protocol, for example 0.25% trypsin with EDTA in Hank's salts (GIBCO-BRL No. 15050). Approximately two days after plating MSCs, the cultures should have about $3 \times 10^6$ cells in toto, and the cells then can be passaged so that, for example, one-tenth of the cells in a near-confluent flask are seeded onto a new substrate.

To differentiate MSCs into a neuronal morphology, any growth factors that stimulate MSC proliferation from the culture typically are withdrawn, and agents are added, such as nerve growth factor (NGF) and retinoic acid (RA), that stimulate cellular differentiation. Exemplary culture conditions for inducing differentiation are disclosed by Ronnet et al., *Science* 248: 603 (1990), and Pleasure et al., *Neuroscience* 12: 1802 (1992), who added 1-isobutyl-3-methyl xanthine (IBMX), dibutyryl adenosine 3',5'-monophosphate (cAMP), and nerve growth factor (NGF), followed by an introduction of RA to the cell culture, some 2 to 4 days later. After RA treatment, the cells can be replated at a lower density. After a period of about two more days, the medium would be replaced, using the same concentration of RA. At this stage, NGF remains a suitable growth factor for effecting neuronal differentiation. In addition, NGF also plays a role in promoting the survival of mature neurons, as reported by Reichardt and Farinas, in MOLECULAR AND CELLULAR APPROACHES INTO NEURAL DEVELOPMENT 220–263 (Oxford Univ. 1997), and may be used accordingly.

When the cells are replated, they should be isolated from the substrate on which they are growing. One approach to this end entails dislodging the cells from the culture flasks by striking the flasks, causing the cells to float. Then the floating cells are washed with medium and replated. A suitable substrate for the cell culture at this juncture is MATRIGEL® (product of Becton Dickinson, Bedford Mass., USA), a basement membrane matrix containing, in addition to growth factors, collagen IV, laminin, entactin, and heparan sulfate proteogycan (perlecan), inter alia. The cells then can be seeded in DMEM high glucose (HG) with FBS and penicillin/streptomycin, supplemented with about 1 μl of cytosine arabinoside, and 10 μl each of fluorodeoxyuridine and uridine.

Yet another approach for effecting differentiation along a neuronal lineage entails introducing the MSCs into a conditioned medium (CM). For example, Henderson et al.,

*Proc. Nat'l Acad. Sci. USA* 78: 2625 (1981), disclose a suitable CM, comprising chicken embryo extract. In accordance with the methodology disclosed by Henderson et al, the culturing process begins by plating cells onto a substrate, which can be a gelatin-coated plastic dish. The culture medium comprises: three parts minimal essential medium, one part medium 199, 10% (vol/vol) heat-inactivated horse serum, 1% chicken embryo extract, 2 mM glutamine, penicillin at 100 units/ml and streptomycin at 100 µg/ml. Quantities of arabinocytosine can be added to kill dividing cells, after a time that will be apparent to one of skill in the art. One to four days later, the medium is removed, and the cells are washed two times with minimal essential medium (Eagles with 2 mM glutamine, penicillin at 100 units/ml and streptomycin at 100 µg/ml). The cells then are placed in fresh ("non-conditioned") minimal essential medium. After one to four more days of culturing, this medium, now "conditioned," is removed, preserved, and replaced by fresh, non-conditioned medium, which in turn is conditioned for about four days. Conditioned media can be stored at 4° C. for several weeks and still conserve its activity.

To induce MSC differentiation along a neuronal lineage, LIF and β-mercaptoethanol should not be present. In the differentiation context, therefore, it is preferable to culture MSCs, in any of the media previously described, without both LIF and β-mercaptoethanol.

When the differentiation process reaches a point that an in vitro culture, according to the present invention, comprises 40% to 60% neurons, further "purification" to a level of virtually 100% neuronal constituency is possible via, for example, a strategy adopted to purify NT2 cells. Kleppner et al., *J. Comp. Neurology* 357:618–632 (1995) provide a suitable "purification" process. This process entails dislodging the neuronal cells with trypsin, followed by replating the cells and feeding them twice in a 1:1 dilution of conditioned medium, comprising DMEM-HG with 5% fetal bovine serum (FBS) (product of Hyclone, Logan, Utah), 1% Penicillin/Streptomycin (JRH) (product of Biosciences, Lenexa, Kans.), and mitotic inhibitors. Suitable mitotic inhibitors include 1 µM uridine, 1 µM 5-fluoro-2'-deoxyuridine (FUDR), and 0.1 µM AraC (product of Sigma, St. Louis, Mo.). About one week after this culturing process, the cell culture should contain about 99% pure post-mitotic neurons.

Monitoring Cellular Development

A regimen for modifying the constituency of trophic factors in a culture medium, thereby favoring a desired lineage for differentiating MSCs, can be determined empirically, by monitoring cellular development over the course of a given protocol, as described above. The concentration of viable cells, as well as the developmental stage of particular cells, likewise can be determined by conventional techniques. For example, a mature neuronal phenotype can be verified if the cells contain a highly polarized neuronal morphology, including an axon and dendrites. In addition, a cell can be identified in culture by virtue of its producing a neuron-specific gene product, such as a neurofilament subunit, tau protein, mictrotubule-associated protein 2 (MAP2), and neural cell adhesion molecules (N-CAMs).

Thus, it would be routine experimentation to expose the cells to an antibody that binds a neuron gene product or otherwise identifies a human neuron per se, and then to ascertain, under selected culture conditions, the concentration of cells that bind the marker. In this way, one can determine the optimal culture conditions for promoting the differentiation of MSCs into neurons. Illustrative of suitable antibodies for this purpose are MOCH-1, M12, T14, RMO93, RMO24, RMO217, and RMO301. Kleppneretal. (1995), supra, and Miyazono et al., *J. Comp. Neurol.* 357: 818 (1995), describe using these antibodies to identify human neuron cells. For instance, MOCH-1 is able to bind human specific epitopes in N-CAMs, which are polypeptides distinctive of neurons. Brummendorf et al., *Curr. Opin. Neurobiol.* 6: 584 (1 996), have reported that, since the discovery of N-CAMs, over one hundred lg domain-containing neural adhesion and recognition proteins have been identified. Like the N-CAMs, these proteins can serve as neuron-specific markers in this context.

The present invention also encompasses the use of more specific markers, if they are needed. Because Parkinson's Disease adversely affects dopaminergic neurons, for instance, markers specific to dopaminergic neurons, such as tyrosine hydroxylase and dopamine β-hydroxylase, are advantageous for detecting dopaminergic neurons produced in culture, according to the invention. Similarly, choline acetyltransferase is a marker for cholinergic neurons, which are affected in patients suffering from Alzheimer's disease, and tryptophan hydroxylase is a marker for seratonergic neurons.

Proliferating and Differentiating Oligodendrocyte Precursor Cells In Vitro

With an appropriate combination of culture medium and trophic factors, MSCs also can be prompted, pursuant to the present invention, to differentiate into oligodendrocytes in vitro. Essentially as described above, the progression of differentiation can be monitored and, hence, the appropriate regimen determined for adding, removing, and/or altering concentrations of trophic factors which facilitate the differentiation process.

After MSCs are isolated from bone marrow and proliferated to a desired culture density, as previously described, the cells can be plated, in serum-free medium, onto poly-D-lysine (PDL)-coated tissue culture, under conditions suitable for oligodendrocyte proliferation and differentiation, as described, for example, by Barres et al. (1994), supra. Thus, the culture can contain DMEM, bovine serum albumin (BSA), selenium, putrescine, thyroxine, tri-iodothyronine, transferrin, progesterone, sodium selenite and the appropriate trophic factors. The bovine serum medium should be prepared with a highly purified, crystalline grade of BSA (Sigma A4161), to avoid contaminating survival factors. Also, the presence of pyruvate (1 mM) helps support the MSCs during the early stages of cell culturing. The temperature should be kept at a range between 30–40° C.

Two groups of trophic factors, cytokines and growth factors, are especially relevant to proliferating and differentiating MSCs into oligodendrocytes. Exemplary of the growth factors used in this context are: platelet derived growth factor (PDGF), including PDGF-α and PDGF-αα; basic fibroblast derived growth factor (bFGF); transforming growth factor α (TGF-α); insulin like growth factor-1 (IGF-1); neurotrophin-3 (NT3); and thyroid hormone. See Barres et al., *Development* 118: 283 (1993), loc. cit. 120: 1097 (1994), and *Glial Cell Development* 71: (1996); Gokhan et al., 16 A Companion to Methods in Enzymology 345–58 (Academic Press, 1998). The cytokines can be chosen, for example, from among: ciliary neurotrophic factor (CNTF); leukemia inhibitory factor (LIF); interleukins 6, 11 and 12 (IL-6, IL-11, IL-12); and colony stimulating factors (CSFs). ld.

Growth factors that are mitogens will promote cellular proliferation but will not induce differentiation. bFGF is a mitogen for oligodendrocytes and their progenitors, and regulates lineage progression. NT-3 and PDGF also are potent mitogens for cells committed to an oligodendrocyte lineage. The proliferative response of oligodendrocytes to PDGF is retained during the Pro-OL stage (see table, below) but is lost by the Pre GalC stage, before the down-regulation of the PDGF α-receptor. IGF-1 accelerates and increases the production of oligodendrocytes in culture, due to enhanced differentiation and, possibly, proliferation, of Pro-OL's. Accordingly, it is believed beneficial to introduce IGF-1 to the culture, beginning at least at the Pro-OL stage.

Thyroid hormone can play an important role in oligodendrocyte development, since its presence affects the differentiation of the oligodendrocyte lineage from its early stages until myelination. Barres et al. (1994), supra. Thyroid hormone will enable a precursor cell to differentiate into an oligodendrocyte in the presence of mitogens. But it is not needed to induce differentiation when no mitogens are present. Id.

In one embodiment of the invention, it is useful to pre-treat the undifferentiated cells with growth factors, such as bFGF and/or PDFG-αα, followed by factor withdrawal and subsequent addition of cytokines. The cytokines can be a combination of those described herein. Throughout oligodendrocyte differentiation, it is important to monitor culture temperatures and keep the temperature within established bounds, that will become apparent to the skilled artisan.

Based upon experiments involving hippocampal and cerebellar progenitor cells from murine fetuses, Gokhan et al. (1998), supra, have reported that cytokines from five separate factor subclasses can be used to program the lineage commitment and cellular maturation of evolving oligodendroglial lineage species. More specifically, a combination of bFGF, PDGF-αα, IGF-1, NT3, and a CNTF/IL-6 subclass member has been elucidated. In addition, gp130-related ligands, for example, CNTF, LIF, IL-11, IL-12, and G-CSF demonstrate an ability to exhibit diverse cellular actions at multiple lineage transitions. Thus, Gokhan et al. have provided insight as to the appropriate combinations of trophic factors that are needed to induce MSC differentiation into oligodendrocytes.

In addition, Barres et al. (1993), supra, have reported the importance of three classes of trophic factors to promote long term survival of oligodendrocytes in vitro: (1) IGFs, (2) neurotrophins, particularly NT-3, and (3) CNTF, LIF and IL-6. The group (3) molecules belong to a family of homologous cytokines. CNTF is another survival factor which promotes oligodendrocyte survival in vivo. That is, it induces oligodendrocyte precursors in culture to express the astrocyte-specific protein GFAP, and it is also a survival factor for purified oligodendrocytes in vitro. Both LIF and IL-6 promote the survival of purified oligodendrocytes. Plateau concentrations of LIF or IL-6 have promoted the survival of about 50% of the purified oligodendrocytes in vitro, as disclosed by Barres et al. (1993).

Neuroblastoma CM, such as B104 CM disclosed by Louis et al., *J. Neurosic. Res.* 31: 193–204 (1992), is another type of medium that is suitable for differentiating MSCs into oligodendrocytes, according to the present invention. To this end, MSCs are isolated from bone marrow, proliferated to a desired culture density on a suitable substrate, and then isolated therefrom, as previously described. The isolated MSCs can be transferred to a substrate, such as a tissue culture dish or glass coverslip (Bellco Glass), that has been coated with about 10 μg/ml of poly-D-lysine, as described above. The substrate additionally may be coated with 1.5 mM borate.

The MSCs can be plated onto the substrate in a medium comprising about 10% fetal calf serum in DMEM with 2 mM glutamine in a penicillin and streptomycin mixture. Preferably, the cells are plated to a density of between about one-half and complete confluency, for example, about 5,000 cells/cm$^2$. After the cells are plated, it is preferable to allow them to adhere to the substrate surface before adding a medium, such as B104 CM, that induces differentiation into oligodendrocyte precursors. This adhesion process will occur spontaneously, typically about 24 hours after plating the MSCs.

When a sufficient concentration of the cells has adhered to the substrate, the cells can be washed with minimal essential medium and cultured in the chosen neuroblastoma conditioned medium. To produce B104 CM medium for this purpose, grow a culture of neuroblastoma cells, such as B104 cells, in DMEM, supplemented with 10% heat-inactivated fetal calf serum (a product of Hyclone, Hogan, Utah; or Sigma, St. Louis, Mo.), 2 mM glutamine, and 100 μg/ml penicillin. When culture reaches a concentration of from about one-half to full confluency, wash them twice with Hank's salt solution, for example, and incubate them in serum-free DMEM, combined with 2 mM glutamine, 100 μg/ml penicillin, and N1 supplement, as described by Bottenstein et al., *Exp. Cell Res.* 125: 183 (1980). The Ni supplement contains: 50 μg/ml transferrin, 5 μg/ml insulin, 100 mM putrecine, 20 nM progesterone, and 30 nM selenium. After about three or four days of culturing, the medium then can be removed, filtered and stored at −20° C., until needed. Preferably, the medium is used within one week.

To induce differentiation of MSCs to oligodendrocyte precursors, MSCs that are isolated and plated, as described, are cultured in a medium comprising about 30% B104 CM by volume in N1 medium. (The N1 medium comprises 5 μg/mL transferrin, 16.1 μg/mL putrescene, 6.3 ng/mL progesterone, 3.3 ng/mL selenium, 10 ng/mL biotin, 2 mM glutamine, and 5 μg/mL insulin in DMEM.) The resultant "B104/N1" medium can be prepared from frozen stock, preferably stored no longer than one week. At this stage, the cell culture should be monitored to detect any cells that have differentiated into, or otherwise resemble, oligodendrocyte precursor cells.

Cellular differentiation of an MSC into an oligodendrocyte precursor cell may occur as soon as about 6 to 12 hours, and readily occurs by about 24 hours after culturing the cells in the B104/N1 medium. An oligodendrocyte precursor cell can be distinguished from other cell types by the presence of small processes in the former cell type, as well as its relative small size and round shape. MSCs, on the other hand, typically are very flat and long, compared to an oligodendrocyte precursor. Alternatively, an oligodendrocyte precursor cell may be distinguished from other cells in culture, by employing conventional immunohistochemical techniques. Suitable antibodies for implementing this process include A2B5 and GD3, as set forth in the table, below. B104 conditioned medium also can induce rapid proliferation of oligodendrocyte precursor cells that have differentiated from MSCs. Accordingly, the continued presence of B104 CM can yield higher concentrations of oligodendrocyte precursors after a portion of MSCs have differentiated into oligodendrocyte precursors.

If the oligodendrocyte precursor cells do not comprise 100% of the culture population, the culture can be subjected to conventional immunopanning techniques, as described, for example, by Grinspan et al., *J. Neurobiol.* 43: 1–17 (2000), to purify the oligodendrocyte precursor cells in culture. This immunopanning purification process entails removing the cells from culture, for example, by trypsinization or trituration in Hanks' solution without calcium or magnesium, followed by pelleting, counting and resuspending the cells in a culture medium. This medium comprises, e.g., Ham's F12 with 10 μg/ml insulin, 30 mM sodium selenite, 10 μg/ml human transferrin, $10^{-11}$ M triiodothyronine, 0.05 μg/ml hydrocortisone, 50× concentrated minimal essential amino acids 10 μg/ml 10× concentrated MEM vitamins, and penicillin and streptomycin (1%vol/vol).

The cells may remain in suspension until they are transferred onto one or more precoated immunopanning dishes, which can be, for example, a non-tissue culture plastic petri dish. The immunopanning dish is coated with a substrate useful for separating the oligodendrocyte precursor cells from the other cells in suspension. Accordingly, before seeding the cells onto the immunopanning dish, the dish is coated with one or more antibodies, at least one of which has an affinity for a cell type within the suspension.

In one embodiment, the immunopanning dish first is coated with a secondary antibody, that is, an antibody that has an affinity for a primary antibody. In this context, a "primary antibody" is an antibody that has an affinity for at least one type of cell within the suspension of cells that is seeded onto the immunopanning dish. The chosen secondary antibody will depend upon the employed primary antibody. For example, the secondary antibody can be an IgG, when the primary antibody is "Ran-2;" or IgM, when the primary antibody is "A2B5" or "04." After the secondary antibody is coated onto the immunopanning dish, the secondary antibody may be incubated therein for about 6–18 hours at 4 C, to allow a sufficient amount of antibody to adhere to the immunopanning dish. The dish then may be washed about 1 to 5 times, e.g., with sterile PBS, to remove any non-adherent secondary antibodies, taking care not to let plates dry out.

Thereafter, a primary antibody can be added to the immunopanning dish and the dish may be incubated for about 1 hour, for example, at about 25 C. Any non-adherent antibody may be removed by washing the immunopanning dish about 1–5 times, preferably twice, with sterile PBS, for example, taking care not to let plates dry out. To this end, the washing solution may be left in the immunopanning dish after the last wash.

After the primary antibody has been coated onto the immunopanning dish, the cells may be seeded onto the dish at a density of about 2–4 million, preferably 2.5–3 million, cells per dish in a medium comprising, e.g., about 8 ml of medium comprising Ham's F12 with supplements, as described above. The composition in the dish can be incubated at about 25 C for an amount of time sufficient to allow the primary antibodies bind the cells. The incubation period may be about 15 minutes to 2 hours, preferably about 30 minutes.

The primary antibody of the dish may be one that does not have an affinity for an oligodendrocyte precursor, but instead has an affinity for other cell type(s) within the suspension. For example, the primary antibody may be Ran-2, which binds rat astrocyte cells or astrocyte precursors and, presumably, can bind human astrocytes. Accordingly, such an antibody would bind "undesirable" cells and/or other contaminants. Thus, the cells not forming a conjugate with the primary antibody would include oligodendrocyte precursors. The non-adhering cells (ie. cells not binding to the primary antibody) can be removed from the dish via conventional techniques and may be transferred to another immunopanning dish.

The new immunopanning dish to which the non-adhering cells are transferred similarly may contain a primary antibody that does not bind oligodendrocyte precursor cells, but instead binds other cells that may be present in the suspension. For example, the primary antibody again may be Ran-2 or another antibody recognizing one or more cell types that are not oligodendrocyte precursors. Ran-2 may be a suitable antibody in this regard, since non-oligodendrocyte precursor cells would have a higher affinity for Ran-2 than an oligodendrocyte precursor cell. As previously described, any cells not forming a conjugate with the primary antibody include oligodendrocyte precursors and can be removed from the dish via conventional techniques and seeded onto another immunopanning dish. The invention provides for one, two, or even further passages of the cells on immunopanning dishes containing a primary antibody that does not bind oligodendrocyte precursor cells, but instead binds other, undesirable, cells and/or contaminants that may be present in the suspension.

The immunopanning dish to which the cells are transferred also may contain a primary antibody that is specific to, or otherwise has an affinity for, oligodendrocyte precursor cells. For example, the primary antibody may be A2B5 or 04, antibody to rat oligodendrocyte precursors, which also recognizes human precursors, as disclosed by Roy et al., *J. Neurosci.* 19: 9986–1003 (1999). After the composition of cells and antibodies are incubated, the primary antibody will have bound oligodendrocyte precursor cells. Any non-adherent material, including the culture medium, can be washed off of the dish. The remaining oligodendrocyte precursor cells can be separated from the primary antibody with a trypsin-versine solution. The unbound oligodendrocyte precursors then may be seeded on a fresh petri dish in a medium comprising the N1/B104 medium, as described above.

The process of differentiating an oligodendrocyte precursor cell into a mature oligodendrocyte normally entails the substitution of the B104 CM with another medium, since B104 CM contains growth factors that likely will hamper further differentiation of an oligodendrocyte precursor. Accordingly, the above-mentioned oligodendrocyte precursors can be isolated from the B104/N1 medium and fed with a medium comprising, for example, 50% DMEM and 50% Ham's F12 with a mixture of transferrin, putrescene, progesterone, selenium, biotin, glutamine, insulin, $T_4$, and glucose ("DMEM/F12 differentiation medium"). In particular, this mixture can comprise 50 μg/mL transferrin, 5 mg/mL putrescene, 3 ng/mL progesterone, 2.6 ng/mL selenium, 10 ng/mL biotin, 2 mM glutamine, 12.5 μg/mL insulin, 0.4 μg/mL T4, and 0.3% glucose. Another suitable medium for differentiating oligodendrocyte precursors into mature oligodendrocyte includes trophic factors CNTF and NT-3, as described above. To this end, CNTF and NT-3 can be added to the DMEM/F12 differentiation medium at 2–5 ng/ml and at 100 ng/ml, respectively.

Astrocyte CM is yet another suitable medium for differentiating the cells of the invention into Oligodendrocytes. Gottlieb et al., Culturing Nerve Cells 517–530 (MIT Press, 1 998), disclose the preparation of this medium, which consists of growing a culture of astrocyte cells in DMEM-BS for 48 hours, collecting the medium, and then replacing the medium with fresh DMEM-BS for another 48 hours. A suitable mixture of approximately 500 ml DMEM-BS contains the following components: 469 ml D-MEM (Gibco BRL No. 11995-065), plus 25 μg/ml gentamicin (Gibco BRL no. 15750-011); 10 ml prepared insulin; 5 ml prepared transferrin; 5 ml glutamine; and 11 ml of a "supplemental mixture." The supplemental mixture can be made in a volume of 444 ml. The first step is to combine: 200 ml PBS+0.72 mL bovine serum albumin (BSA) path-o-cyte 4 (ICN Biochemicals, St. Louis, Mo.); 200 ml $H_2O$+322 mg putrescine (Sigma no. P-7505); 20 ml ethanol (EtOH)+8.0 mg thyroxine ($T_4$, Sigma no. T-2501); and 20 ml EtOH+6.74 mg triiodothyronine ($T_3$, Sigma no. T-2752). If a thyroid hormone-free medium is needed, $T_3$ and $T_4$ can be substituted with corresponding amounts of EtOH. Next, add 2 ml each of 20 ml EtOH+12.46 mg progesterone (Sigma No. P-0130), and 20 ml $H_2O$+7.74 mg selenium (Sigma No. S-1382). This entire mixture is then filtered through a 0.22 μm filter and can be separated into 11 ml aliquots, stored at −20° C. Prepared transferrin, mentioned above, is obtained by mixing 10 mg/ml transferrin (Sigma No. T-2252) in double-distilled water, followed by a filtration step. Prepared insulin is made by pre-diluting 200 mg insulin (Sigma No. I-5500) in 100 mL $H_2O$, then adding HCL (1N/ca. 10 ml) until the insulin dissolves. After filtering the mixture through a 0.22 μm filter, add sterile water to a final volume of 400 ml.

Monitoring Cellular Development

As previously mentioned, the need to add, remove and/or alter the concentration of trophic factors can be determined empirically by monitoring cellular development in a particular protocol. In this context, the concentration of viable cells, as well as the developmental stage of particular cells, can be determined by techniques known in the art.

For example, the concentration of viable cells in vitro can be monitored by the MTT survival assay, as described in Barres et al. (1 993), supra. According to this process, 3-(4,5-dimethylthiazol-2-yl)-2,5-diphenyl tetrazolium bromide (MTT, product of Sigma) is dissolved in PBS sterilized by passage through a Millipore filter (0.22 μm). This stock solution is added to the cultures for about 1 hour at 37° C. Viable cells with active mitochondria cleave the tetrazolium ring to form a visible dark blue formazzan reaction product. The percentage of viable cells can be counted by bright-field phase microscopy.

In addition, it is useful to determine the developmental staging of oligodendrocyte precursor cells under particular culture conditions, because different developmental stages may require different concentrations of trophic factors, as well as other changes to the protocol. Any of the known markers that are specific for a particular oligodendrocyte-precursor stage can be considered for use in tracking cellular differentiation in vitro, for example, by known immunohistochemistry techniques.

Thus, MSCs and/or MSC-differentiated cells can be cultured on glass coverslips under different culture conditions, characterized by varied quantities of trophic factors. After culturing the cells, pursuant to empirical regimen described above, the cells are fixed and then treated with antiserum, in order to detect the presence of a specific marker (see table below), corresponding to an oligodendrocyte developmental stage. Information thus gained will aid in determining culture conditions that are optimal for MSC differentiation to mature oligodendrocytes.

Pfeiffer et al., *Trends in Cell Biol.* 3: 191 (1993), disclose various stage-specific markers which can be used to identify the known stages of oligodendrocyte development. These developmental stages, and markers identifying each stage, are shown in the following table:

| Pre-GD3 | GD3 (O2A) | Pro-OL | Pre-GalC | Immature OL | Mature OL |
|---|---|---|---|---|---|
| PSA-NCAM | GD3 | POA (o4/acO7) | r-Ag (R-Mab) | Galc (R-Mab, 01) | GalC |
| Vim | A2B5 | A2B5 | POA | SUL (04/A007, R-Mab) | SUI |
| | Vim | GD3 | GD3$^+$→ GD3$^-$ | CNP | CNP |
| | SCIP | Vim | Vim$^+$→ Vim$^-$ | | PLP |
| | | | SCIP$^+$→ SCIP$^-$ | | MBP |
| | | | | | MOG |

More specifically, this table details the known stages of oligodendrocyte development, coupled with stage-specific markers at these different stages; antibodies identifying some markers are shown in parentheses. The earliest stage is Pre-GD3 (Pre-O-2A), when the cells are proliferating and monopolar, expressing the embryonic neural cell adhesion molecule. Cells at this stage differentiate into proliferative, migratory bipolar GD-3 (O-2A) cells. O-2A precursor cells express gangliosides recognized by the monoclonal antibodies (Mabs) GD3 and A2B5. The Pro-oligodendroblast (Pro-OL) stage, next in the oligodendrocytic developmental lineage, is characterized by multipolar, post-migratory, proliferative cells which can be identified by reaction with two Mabs, O4 and AOO7, which recognize the sulphated surface antigen POA. The transient Pre-GalC developmental stage follows, identified by the ability of this precursor cell to react with the Mab R but not the anti-GalC Mab O1. The onset of the immature OL stage is identified by the synthesis and transport of GalC and sulphatide to the cell surface, as well as the synthesis of 2'-3'-cyclic nucleotide 3'-phosphohydrolase (CNP). Mature oligodendrocytes develop with the regulated expression of markers such as proteolipid protein (PLP), myelin basic protein (MBP), and myelin/oligodendrocyte glycoprotein (MOG). Accordingly, these stage-specific markers provide powerful tools for deducing optimal culture conditions at each oligodendrocytic developmental stage.

Immortalizing MSCs

The present invention also encompasses the creation of a cell line of immortalized MSCs, thereby to increase cell life and the supply of MSCs. Conditionally immortalizing MSCs would provide an infinite, renewable supply of homogenous human cells capable of differentiating into cell lines herein disclosed, maximizing the yield of cells in vitro.

Initially, the cells are plated on a surface that does not substantially inhibit proliferation. MSCs may be conditionally immortalized by transfection or infection of the plated cells with a suitable vector containing a growth-promoting gene, i.e., a gene coding for a protein that, under appropriate conditions, promotes growth of the transfected cell, such that the production and/or activity of the growth-promoting protein is regulatable by an external factor. In one embodiment, the growth-promoting gene is an oncogene, such as the myc gene, the SV40 large T antigen gene, and a mutant p53 gene (see WO 98/10058). In another embodiment, the 2 kD catalytic fragment of the telomerase gene (hTERT), as reported by Myerson et al., *Cell* 90: (1

997) (see GenBank Accesion No. AFO 18167), is placed under the control of a regulatable promoter. See also de Lange et al., *Science* 283(5404):947–9 (1999).

Transfection of an MSC with an exogenous gene may be achieved by a variety of conventional methods, including but not limited to retroviral or adenoviral infection, electroporation, and calcium phosphate-facilitated uptake of exogenous DNA. After MSCs are transfected, they can be maintained and differentiated into oligodendrocytes and neurons, respectively, by creating the culture conditions described herein.

Accordingly, the invention contemplates delivering to an MSC a vector (e.g. a retroviral construct) that contains a DNA molecule capable of encoding hTERT. The invention also provides for delivering to an MSC a gene that encodes a protein suitable for toxin selection (e.g. a neo resistance or Hygromycin resistance gene). The toxin selection gene can be employed, according to conventional technology, to isolate any MSC that has integrated into its genome the toxin selection gene and, thus, the immortalizing gene. For instance, transduced MSCs that are not killed by a toxic agent, e.g. Hygromycin, form polyclonal foci. Another characteristic indicative of a transduced MSC is rapid proliferation of the MSC, vis-à-vis an MSC that does not express an immortalizing gene. Once isolated, the population of infected cells preferably contains few, if any, MSCs that do not express an immortalizing gene, such as hTERT. Once immortalized, an MSC can be differentiated into either an oligodendrocyte or neuronal lineage, according to the methodology disclosed herein.

The invention also provides for infecting an MSC with one or more additional exogenous DNA molecules, in conjunction with h-tert. For instance, immortalizing a human MSC may require the activation of an oncogene (e.g. H-ras, T-antigen, or myc) and also may require the suppression of one or more proteins that inhibit proliferation, such as a tumor suppressor gene (e.g. p53).

Still further, the invention contemplates the transfection or infection of an MSC with other types of exogenous genes. For instance, in the context of gene therapy, discussed in detail below, an immortalized MSC can be transfected with an exogenous DNA molecule that encodes, for example, a needed neurotransmitter.

Treating Patients With CNS Disorders

Treating a subject with a CNS disorder can entail, according to the present invention, intracerebral grafting of MSCs or MSC-differentiated cells to the CNS, including the region of the CNS having the disorder. MSC-differentiated cells include, for example, oligodendrocyte precursors that have been differentiated by culturing MCSs in a medium comprising B104 CM. The cells of the invention can be injected into a number of sites, including the intraventricular region, the parenchyma (either as a blind injection or to a specific site by stereotaxic injections), and the subarachnoid or subpial spaces. Specific sites of injection can be portions of the cortical gray matter, white matter, basal ganglia, and spinal cord. In principle, any animal affected by a CNS disorder, as described above, can be so treated by one or more of the methodologies described herein.

Conventional techniques for grafting are described, for example, in Neural Grafting in the Mammalian CNS, Bjorklund and Stenevi, eds. (1985), the contents of which are incorporated by reference. Procedures include intraparenchymal transplantation, achieved by injecting the cells of the invention into the host brain tissue. However, transplantation of the cells of the invention can be effected in a number of CNS regions.

Pursuant to the invention, administration of cells into selected regions of a subject's brain may be made by drilling a hole and piercing the dura to permit the needle of a microsyringe to be inserted. Alternatively, the cells can be injected intrathecally into a spinal cord region. A cell preparation of the invention permits grafting of cells to any predetermined site in the brain or spinal cord. It also is possible to effect multiple grafting concurrently, at several sites, using the same cell suspension, as well as mixtures of cells from different anatomical regions.

Treatment of a subject, according to the invention, can take advantage of the migratory ability of MSCs, using them to provide a peptide, protein or other substance to a region of the CNS affected by a dysfunction or deficiency relating to that substance. To this end, the cells of the invention (including an MSC that has differentiated into a mature neuron) may contain exogenous DNA encoding a product that is missing in a patient suffering from a CNS disorder. For example, the DNA can code for a transmitter, such as acetylcholine or GABA, or a receptor for such a transmitter. If a patient is suffering from a glutamate-induced injury, it may be desirable to introduce into the patient a gene coding for a glutamate transporting protein, which can reduce glutamate-induced cytotoxicity. Other transmitters, such as dopamine, adrenaline, noradrenaline, epineprine, norepinephrine and serotonin, require multiple enzymes, encoded by different genes, to be synthesized.

In a further approach, DNA that encodes a growth factor or a cytokine can be transfected to MSCs, which then are administered to a patient suffering from a CNS disorder, the etiology or elaboration of which is associated with a deficit or dysfunction in the gene expression product. To this end, the invention contemplates, for example, the use of a gene that, upon expression, produces NGF, brain-derived neurotrophic factor (BDNF), glial cell line-derived neurotrophic factor (GDNF), IGF-1 or CNTF. In addition, the selected gene can encode LIF or any other of the other cytokines, disclosed, for example, by Reichardt and Farinas (1 997), supra, that promotes cell survival or differentiation.

A therapeutic procedure according to the present invention can be effected by injecting cells, preferably stereotaxically, into the cortex or the basal ganglia. Thereafter, the diffusion and uptake of a required ligand that has been secreted by an MSC would be beneficial in alleviating the symptoms of a disorder where the subject's neural cells are defective in the production of such a gene product. Thus, an MSC genetically modified to secrete a neurotrophic factor, such as nerve growth factor (NGF), could be used to prevent degeneration of cholinergic neurons that might otherwise die without treatment. Alternatively, MSCs to be grafted into a subject with a disorder characterized by a loss of dopamine neurons, such as Parkinson's disease, can be modified to contain exogenous DNA encoding L-DOPA, the precursor to dopamine.

According to the present invention, other CNS disorders likewise can be treated, including Alzheimer's disease, ganglioside storage diseases, CNS damage due to stroke, and damage in the spinal cord. For example, Alzheimer's disease is characterized by degeneration of the cholinergic neurons of the basal forebrain. The neurotransmitter for these neurons is acetylcholine, which is necessary for their survival. Engraftment of an MSC containing an exogenous gene, for a factor that would promote survival of these neurons, can be accomplished by the method of the invention, as described.

In another embodiment, the cells of the invention can be transfected with a gene capable of down-regulating a patient's immune response and then administered to a patient in accordance with one of the methods described herein. This type of therapy is useful to treat inflammatory diseases, such as multiple sclerosis. A suitable gene, according to this embodiment, is one that encodes an anti-inflammatory cytokine, such as IL-4 or IL-10. Alternatively, the gene can be an inhibitor of a pro-inflammatory cytokine. Interferon beta (IFN-β) is yet another candidate for treating inflammatory disease. For example, Khademi et al, *J. Neuroimmunol.* 103: 202 (2000), report that IFN-β is able to stimulate anti-inflammatory cytokines (e.g. IL-4 and IL-10) and inhibit pro-inflammatory cytokines, such as interferon gamma (IFN-γ) and tumor necrosis factor alpha (TNF-α).

The following examples are intended to illustrate but not limit the invention. While they are typical of those that might be used, other procedures known to those skilled in the art may be used.

EXAMPLE 1

Preparation/Isolation of Rat Mesenchymal Stromal Cells (MSCs) From Bone Marrow

For isolation of rat MSCs, tibias and femurs were dissected from 8–12 week-old rats. The ends of the bones were cut, and the marrow was extruded with 5 ml of DMEM (GIBCO/BRL) by using a needle and syringe. Between 100 and $200\times10^6$ whole marrow cells were plated on 175 cm$^2$ tissue culture flask in DMEM/10% FBS. After 24 hours, the non-adherent cells were removed by replacing the medium. The medium was replaced every 2–3 days as the cells were grown to confluency. The cells were lifted by incubation with 0.25% trypsin and 1 mM EDTA, passed three of four times.

EXAMPLE 2

Preparation/Isolation of Human MSCs From Bone Marrow

Human MSCs were grown from aspirates taken from the iliac crest of normal males and female volunteers. Aspirates were diluted 1:1 with alpha-MEM/10% fetal bovine serum (FBS) and centrifuged through a density gradient (Ficoll-Paque Plus; 1.077 g/ml; Pharmacia) for 30 minutes at $1,000\times G$. The supernatant and interface were combined, diluted to about 40 ml with alpha-MEM/10% FBS, and centrifuged. The nucleated cells were suspended at a concentration of $1\times10^7$/ml in alpha-MEM/10% FBS and plated at $3\times10^6$/cm$^2$ in 25 cm$^2$ culture dishes. The cells are incubated for three days, and the non-adherent cells are removed by replacing the medium. After the cultures reach confluency, the cells are lifted by incubation with 0.25% trypsin and 1 mM EDTA at 37°C for 3 to 4 minutes. The cells are diluted, 1:2 or 1:3, and then replated. The procedure is repeated for 3 to 5 passages. Beginning with the second passage, 5 ng/ml of platelet-derived growth factor alpha alpha (PDGF-AA; GIBCO/BRL) is added to the medium.

EXAMPLE 3

Human MSCs Were Administered to Newborn Rats Without Immune Rejection

Human MSCs were infected with a virus that expressed bacterial Lac Z and green fluorescent protein (GFP). Flax et al., *Nature Biotech*, 16: 1033 (1 998), disclose a method for infecting cells in this fashion. About 50,000 human MSCs were injected into the lateral ventricles of newborn rats, following methodology such as that disclosed in Flax et al. (1998), supra. The rats were killed at varying intervals and the brain sections were stained for β-galactosidase activity (product of the Lac Z gene). Many cells had integrated into the nervous system of the rats and stained blue (product of the β-galactosidase activity). Further, there were no obvious signs of immune rejection. Thus, transplantation was effected, in young animals, without any immediate concerns of immune rejection.

EXAMPLE 4

Human MSCs Expressed the Potential to Differentiate Into Oligodendrocytes Upon Being Administered to Myelin-deficient Rats Myelin deficient (MD) rats have a genetic defect in the proteolipid protein (PLP) gene, resulting in an inability to form myelin in the CNS. As a result, these animals die at three weeks of age. On the order of 50,000 cells were injected into the lateral ventricles of newborn rats, using techniques well-known in the art, to test whether MSCs can differentiate into oligodendrocytes.

One and two weeks after transplantation, both affected (tested by tail clip analysis of the DNA) and normal rats were killed and their brains were examined by light microscopy. Using Luxol fast blue staining, it was apparent that some myelin was present in the MD rats. Also, indirect immunofluorescence analysis revealed the expression of PLP, which is normally absent in the injected MSCs and in the host cells (due to the mutation of the PLP gene). The finding that these cells express human PLP is consistent with the notion that human MSCs differentiated into oligodendrocytes.

EXAMPLE 5

Human MSCs Display Capability for Differentiating Into Neurons, Upon Being Administered to Newborn Rats As in example 4, human MSCs were infected with a virus that expressed bacterial Lac Z and green fluorescent protein (GFP). About 50,000 human MSCs were injected into the lateral ventricles of newborn rats. When the animals were killed and the brains examined, there were cells expressing β-galactosidase, and it appeared that there were cells with a neuronal morphology. Immunoperoxidase studies were performed on the tissue sections, to confirm that these cells were human neurons. The antibody chosen for this purpose was a monoclonal antibody, MOC1, that recognizes an epitope on human neurons. In examining the section after staining with MOC1, there were a few cells that were MOC1-positive, indicating that there were human neurons in the rat brains which originated from the human MSCs.

EXAMPLE 5

Rat MSCs Were Immortalized by Retroviral Infection With hTERT

Passage 2 MSCs (Osirus) were plated at 50% confluence and infected for six hours with retrovirus pBABE hygromycin hTERT (packaged in PA317 protein envelope) in a 37° C. humidified incubator. After infection, cells were washed 3× with Phosphate buffered saline and placed in culture media. (alpha MEM, supplemented with 10% Fetal Bovine Serum (Atlanta Biologicals) and 2 mM L-Glutamine (Gibco BRL). After 4 days, selection agent Hygromycin was added to the culture media at a concentration of 50 micrograms/mL. After several weeks, polyclonal colonies were isolated, expanded and assayed via RT-PCR for hTERT transcipt. A population of cells within these foci were uniform in morphology and were capable of forming adipoctes, which is the default pathway of differentiation for MSCs. RT-PCR data confirm increased message levels of hTERT in these rapidly growing rat MSCs. The data strongly suggest that immortalized MSCs are capable of differentiation into various lineages.

What is claimed is:

1. A method for differentiating a mesenchymal stromal cell into an oligodendrocyte precursor cell, comprising (i) providing a composition in vitro that consists essentially of said mesenchymal stromal cells and a physiologically compatible carrier, (ii) and culturing said cells in a medium comprising a neuroblastoma conditioned medium, wherein said culturing step provides oligodendrocyte precursor cells capable of differentiating into oligodendrocytes.

2. A method according to claim 1, wherein said neuroblastoma conditioned medium is B104 conditioned medium.

3. A method for differentiating a mesenchymal stromal cell into an oligodendrocyte, comprising (i) carrying out the method according to claim 2, and (ii) exposing said oligodendrocyte precursor cells to conditions such that at least a portion of said oligodendrocyte precursor cells differentiate into oligodendrocytes.

4. A method according to claim 3, wherein step (ii) comprises isolating the oligodendrocyte precursor cells from the B104 conditioned medium.

* * * * *